United States Patent [19]

Maham et al.

[11] 4,131,773
[45] Dec. 26, 1978

[54] APPARATUS FOR DETECTING PRESENCE OF OIL IN A BODY OF WATER

[75] Inventors: Robert M. Maham, Beaumont, Tex.; Matthew D. Beasley, Plainsboro, N.J.

[73] Assignee: Texaco Inc., New York, N.Y.

[21] Appl. No.: 800,368

[22] Filed: May 25, 1977

Related U.S. Application Data

[63] Continuation-in-part of Ser. No. 669,776, Mar. 24, 1976, abandoned.

[51] Int. Cl.² ............................................. H01H 29/00
[52] U.S. Cl. ................................................. 200/61.05
[58] Field of Search .......................... 200/61.04, 61.05; 340/235, 236; 73/73, 76, 61 R, 61.1 R; 338/33, 34, 38

[56] References Cited

U.S. PATENT DOCUMENTS

| 3,800,219 | 3/1974 | Fosberg | 340/236 X |
| 3,918,034 | 11/1975 | Orth, Jr. | 340/236 |

FOREIGN PATENT DOCUMENTS 1399477  4/1965  France ...................................... 324/65

Primary Examiner—James R. Scott
Attorney, Agent, or Firm—Thomas H. Whaley; Carl G. Ries; Henry C. Dearborn

[57] ABSTRACT

A simple apparatus for use in detecting the presence of oil in a body of water. It employs a floating structure which includes at least one pair of electrodes that are immersed in the water. At least one electrode is surrounded by an absorbent oleophilic material so that an electric measurement employing the electrodes will provide an indication of the presence of oil in the body of water.

5 Claims, 3 Drawing Figures

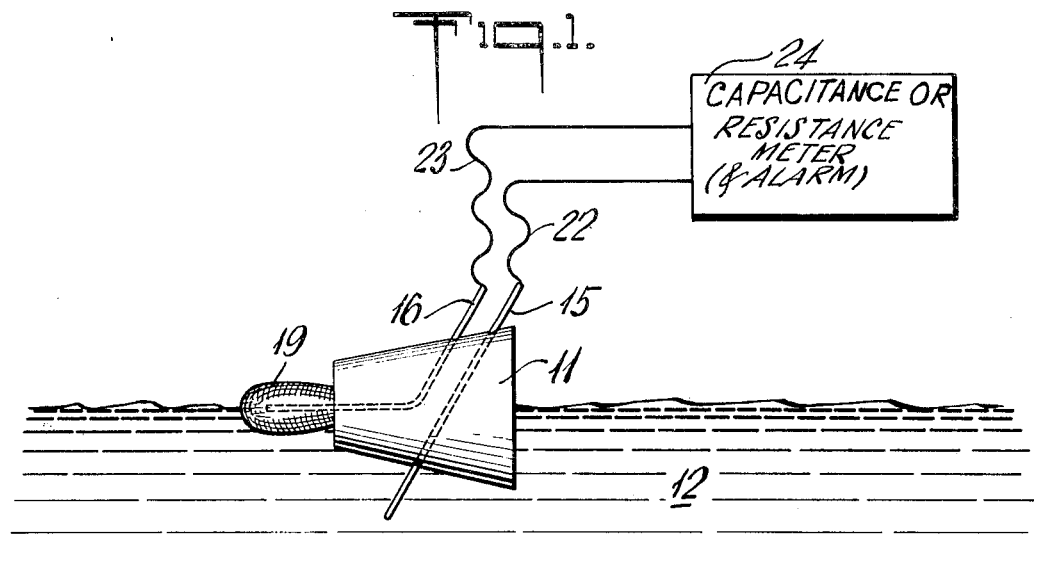
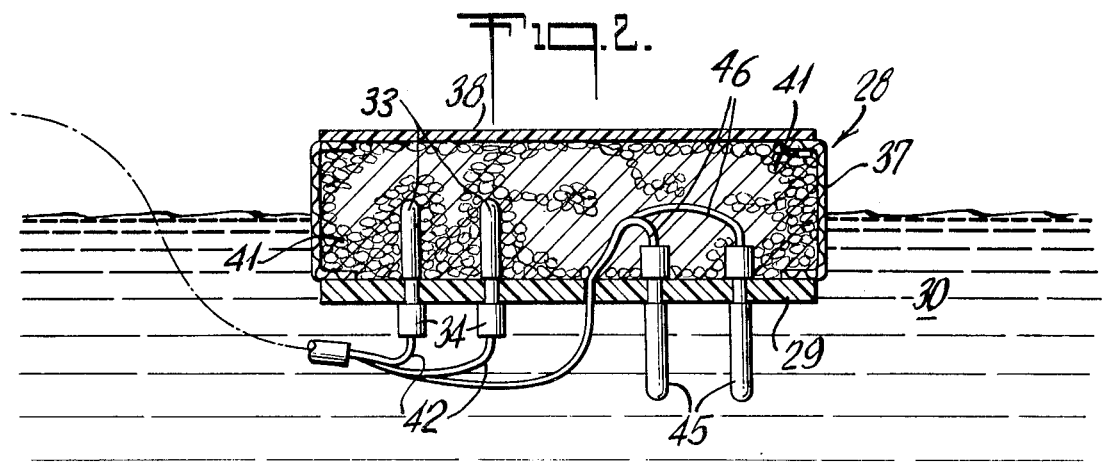
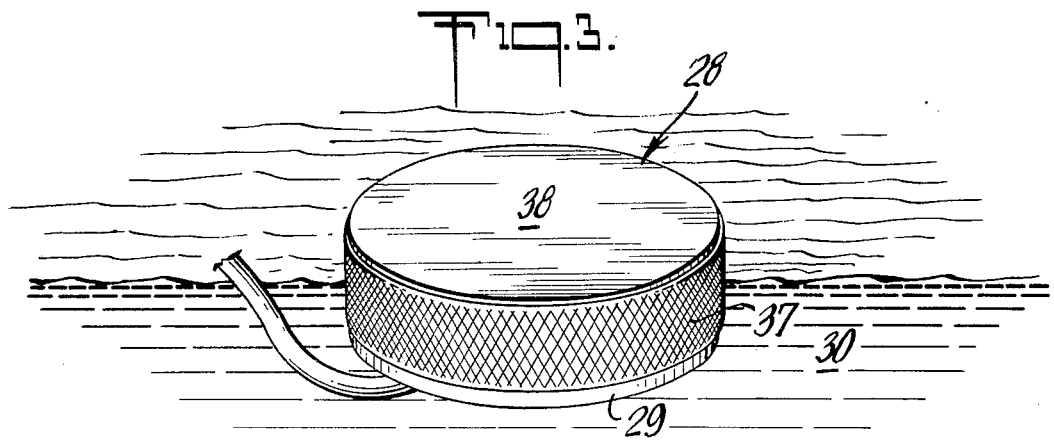

in FIG. 2.

APPARATUS FOR DETECTING PRESENCE OF OIL IN A BODY OF WATER

CROSS REFERENCE TO RELATED APPLICATION

This application is a continuation-in-part of application Ser. No. 669,776 filed Mar. 24, 1976 now abandoned.

BACKGROUND OF THE INVENTION

Field of the Invention

This invention concerns oil detection apparatus in general. More specifically it deals with a simple yet effective apparatus combination that is for use in detecting the presence of oil in a body of water.

Description of the Prior Art

It is well known that oil and water have different electrical properties. Furthermore, there are a substantial number of proposals which have been made heretofore in regard to various apparatus combinations that are intended for use in detecting the presence of oil in water. However, the known prior arrangements are relatively complicated mechanically. Consequently, they are subject to possible malfunction, and in addition they are subject to the fact that they are in varying degree quite costly to manufacture.

Furthermore, a somewhat simpler prior arrangement (see U.S. Pat. No. 3,427,869 N. G. R. Karlbom Feb. 18, 1969) made use of only the physical properties of a material that attracts oil in preference to water, and it failed to make use of any electrical property of oil as opposed to water.

Consequently, it is an object of the present invention to provide a greatly simplified, yet highly effective combination that may be employed in detecting the presence of oil in a body of water.

SUMMARY OF THE INVENTION

Briefly, the invention concerns apparatus for detecting presence of oil in a body of water. It comprises in combination a floating body of electrically insulating material. It also comprises a pair of electrodes mounted on the floating body and adapted for being in contact with the water and having exposed surfaces for making contact with water, and oleophilic means covering all of exposed surfaces of at least one of the electrodes. The oleophilic means comprises an absorbent mass of oleophilic material whereby presence of oil will be detected by being concentrated between and by replacing water in between the electrodes.

Once more briefly, the invention concerns apparatus for detecting presence of oil in a body of water. It comprises in combination a housing having an electrically insulating material base and a first pair of electrodes mounted on the base and extending into the interior of the housing, and a pervious exterior on the housing for permitting free passage of water therethrough. The housing interior contains a plurality of oleophilic beads surrounding and contacting all of the exposed surface of the first pair of electrodes. It also comprises a second pair of electrodes mounted on the base and extending outside of housing into body of water, and a pair of insulated flexible electric conductors connected to each of the pairs of electrodes for making electrical circuit connections therewith. The apparatus combination is lighter than water and is designed for floating with the pervious exterior at least partially submerged.

BRIEF DESCRIPTION OF THE DRAWINGS

The foregoing and other objects and benefits of the invention will be morefully set forth below in connection with the best mode contemplated by the inventors of carrying out the invention, and in connection with which there are illustrations provided in the drawings, wherein:

FIG. 1 is a schematic illustration showing one form of apparatus according to the invention;

FIG. 2 is a cross-sectional view illustrating a different form of apparatus according to the invention; and FIG. 3 is a perspective view of the apparatus shown in FIG. 2.

DESCRIPTION OF THE PREFERRED EMBODIMENT

While there has been much recent concern with pollution of water by oil spills or other sources of oil contamination, heretofore the various proposals for detecting the presence of oil have been relatively complicated and consequently have involved considerable expense. On the other hand, this invention provides apparatus that is quite simple and basic, particularly as to mechanical structure, so that the cost thereof should be minimal. In addition, it has been discovered that the structure as proposed by this invention is highly effective for making an electrical determination which will indicate the presence of oil in a body of water.

With reference to FIG. 1 it is to be noted that a simplified version of this invention is illustrated. It involves a floating body 11 that is made of electrically insulating material, e.g. cork or the like. This body 11 being lighter than water will float on the surface of a body of water 12.

In order to detect the presence of oil in the body of water 12, there are a pair of electrodes 15 and 16 which are supported by the floating body 11. These electrodes may be made of any feasible conducting material, e.g. copper or the like, and it will be noted that electrode 15 may be a straight rod which extends through the body of the cork 11. It extends out underneath the cork 11 beneath the surface of the body of water 12. The other electrode 16 is inserted into and changes direction within the body 11 so that it comes out close to the surface of the water 12. Then, in order to increase the effectiveness of the oil detection, there is an absorbent mass of oleophilic material 19 that is wrapped around and covers the entire exposed end of the electrode 16 which extends out from the body 11 of the apparatus. It will be understood that there are various known oleophilic materials which are commercially available. For example, there are materials that are characterized generally as "sorbents" which have the desired attributes and that are manufactured by such companies as the 3M Company, Saint Paul, Minn.; Innova, Seattle, Wash.; and the Dow Chemical Co., Midland, Mich.

Electrically connected to the electrodes 15 and 16 there are conductors 22 and 23 respectively, which are connected to a capacitance or resistance meter 24. It will be appreciated that the resistance or capacitance meter measurement may be connected to some arrangement for providing an alarm (as indicated by the caption) if desired. Furthermore, it will be understood by anyone skilled in the art that the electrical circuit for making the resistance measurement may take various forms and the arrangement thereof is not part, per se, of this invention.

In addition, it will be understood by anyone skilled in the art that the electrical characteristics being measured between the electrodes 15 and 16 might be other than resistance. For example, capacitance or some other electrical characteristic might be measured depending upon the electrical circuit that it is desired to employ in the measurement made by meter 24.

It will be appreciated that in operation the absorbent material 19 will draw the liquid into contact with the covered end of electrode 16. That liquid will be water unless there is some oil in the body of water 12. In the latter event, of course, the oleophilic material 19 will tend to attract the oil to the exclusion of the water. Therefore the water in the absorbing pores is replaced and consequently the electrical property, e.g. resistance between the electrode 16 and the other electrode 15 via the liquids (i.e. where they are immersed in the body of water 12) will change because the electrical resistance of oil is much greater than that of water. Such change will, of course, be adequate to provide an indication that shows the presence of the oil, and as already indicated such indication may be employed to provide for an alarm if desired.

In FIGS. 2 and 3 there is illustrated another embodiment of an apparatus combination according to the invention. In this case there is a housing 28 that is circular in shape and includes a base 29 which is constructed of electrically insulating material that is light enough to cause the entire apparatus to float on a body of water 30. There are a first pair of electrodes 33 that are mounted on the base 29 in any feasible manner, e.g. by extending through a pair of holes therein. These electrodes 33 have a pair of collars 34 on the outside of the base 29 to hold the electrodes 33 in place. Obviously, the collars 34 will be made of electrically insulating material.

It will be observed that the electrodes 33 extend upwardly from the base 29 into the interior of the housing 28 which is made up of a pervious exterior 37. This may take the form of screening as indicated in the drawings. This exterior 37 is attached at the top edge thereof to a thin plate 38 so as to enclose the interior. The interior is filled with a plurality of oleophilic beads 41 which surround the electrodes 33 in contact therewith. They will act in an absorptive manner as to the water in which the apparatus is floating. Consequently whenever oil is found in or on the body of water 30 it will be absorbed by the beads 41, and being oleophilic they will attract such oil to the exclusion of the water and consequently the electrical resistance between the electrodes 33 will change in the presence of such oil.

Again, it will be understood that the oleophilic beads may be a commercial product such as that manufactured by Dow Chemical Co., Midland, Mich. 48640 which is called "Imbiber Beads".

It will be understood that there are a pair of electrical conductors 42 that make electrical connections with the electrodes 33. Such conductors are, of course, insulated from the water 30 so that the electrical affect to be measured will be only that existing between the pair of electrodes 33.

In this apparatus there is in addition to the measuring electrodes 33, a similar pair of electrodes 45 that are mounted on the base 29 in a manner like electrodes 33. However, electrodes 45 are mounted in the reverse manner such that they extend downward from the base 29 into the body of water 30. These electrodes 45 have a pair of electrical conductors 46 that are insulated in a similar manner as the conductors 42. They are connected to an electrical circuit (not shown) for making the desired measurement to determine the presence of oil. It will be understood by those skilled in the art that the electrodes 45 are desirable for making a reference measurement of the resistant or other electrical property of the body of water 30. Then any change in such characteristic may be compensated for, and the measurement indicating oil (as determined by the other pair of electrodes 33) will be more accurate and not subject to changes in the characteristics of the entire body of water 30.

It will be noted that the apparatus according to this invention is compact and simple, and will be quite free of any mechanical difficulties because there are no moving parts involved.

While particular embodiments of the invention have been described above in considerable detail in accordance with the applicable statutes, this is not to be taken as in any way limiting the invention but merely as being descriptive thereof.

We claim:

1. Apparatus for detecting presence of oil in a body of water, comprising in combination
   a floating body of electrically insulating material,
   a pair of electrodes mounted on said floating body and adapted for being in contact with said water and having exposed surfaces for making contact with said water, and
   oleophilic means covering all of said exposed surfaces of at least one of said electrodes,
   said oleophilic means comprising an absorbent mass of oleophilic material whereby said presence of said oil will be detected by being concentrated between and by replacing water in between said electrodes.

2. Apparatus according to claim 1, further comprising
   flotation means for supporting said electrodes immersed in said water near the surface of said body of water.

3. Apparatus according to claim 2, wherein
   said floation means comprises a base supporting a housing containing a plurality of oleophilic beads,
   said electrodes being mounted on said base in said housing and covered by said beads.

4. Apparatus according to claim 3, further comprising
   a second pair of electrodes mounted on said base and extending outside of said housing into said body of water.

5. Apparatus for detecting presence of oil in a body of water, comprising in combination
   a housing having an electrically insulating material base and a first pair of electrodes mounted on said base and extending into the interior of said housing,
   a pervious exterior on said housing for permitting free passage of said water therethrough,
   said housing interior containing a plurality of oleophilic beads covering and contacting all of the exposed surfaces of said first pair of electrodes,
   a second pair of electrodes mounted on said base and extending outside of said housing into said body of water, and
   a pair of insulated flexible electric conductors connected to each of said pairs of electrodes for making electrical circuit connections therewith,
   said apparatus combination being lighter than water and being designed for floating with said pervious exterior at least partially submerged.

* * * * *